United States Patent [19]

Vogel et al.

[11] Patent Number: 5,655,681

[45] Date of Patent: Aug. 12, 1997

[54] THERMAL INSULATING CONTAINER FOR LIQUIFIED GAS

[75] Inventors: Herman Vogel, Newtown; Donald G. Mackay, Roxbury, both of Conn.

[73] Assignee: The Perkin-Elmer Corporation, Norwalk, Conn.

[21] Appl. No.: 724,432

[22] Filed: Oct. 1, 1996

Related U.S. Application Data

[63] Continuation of Ser. No. 524,553, Sep. 7, 1995, abandoned.

[51] Int. Cl.$^6$ .................................................. B65D 90/04
[52] U.S. Cl. ........................ 220/422; 220/423; 220/426
[58] Field of Search .................................. 220/421, 422, 220/423, 426

[56] References Cited

U.S. PATENT DOCUMENTS

| | | | |
|---|---|---|---|
| 3,263,484 | 8/1966 | Watson et al. | 73/15 |
| 3,379,330 | 4/1968 | Perkins, Jr. | 220/423 |
| 3,416,693 | 12/1968 | Covington et al. | 220/423 |
| 3,514,006 | 5/1970 | Molnan | 220/423 |
| 3,525,452 | 8/1970 | Hofmann | 220/423 |
| 5,063,651 | 11/1991 | Kneip, Jr. et al. | 220/423 |

*Primary Examiner*—Joseph M. Moy
*Attorney, Agent, or Firm*—David Aker; Herbert S. Ingham

[57] ABSTRACT

A thermally insulated calorimeter includes a vessel with a chamber containing liquid nitrogen. The vessel is formed of four walls arranged proximately in parallel, each pair of adjacent walls delimiting a space. An inner wall forms the chamber, two partition walls are between the inner wall and an outer wall which is exposed to atmosphere. Each space contains a gas at atmospheric pressure. Each spacing is selected to minimize heat transfer from the atmosphere to the inner chamber, by establishing a maximum spacing for which the air is stagnant. A cover for the vessel has a set of walls with spacings similar to those of the vessel. Sealing for such spacing is provided for a removable main cover and a removable top cover for the calorimeter sample block.

25 Claims, 2 Drawing Sheets

THERMAL INSULATING CONTAINER FOR LIQUIFIED GAS

This application is a continuation of application Ser. No. 08/524,553 filed on Sep. 7, 1995 now abandoned.

This invention relates to containment of liquified gas such as liquid nitrogen, and particularly to a thermal insulating system for such containment, and more particularly to a calorimeter incorporating such a system.

BACKGROUND

Insulating containers are employed in the handling, storage and use of liquified gases such as liquid nitrogen, oxygen, hydrogen and helium. The very low temperatures, for example $-196°$ C. (77 K) for nitrogen, require effective insulating barriers to prevent heat incursion and consequential vaporization and loss of the liquified gas. Another common problem is that the outer surface of the containers becomes cold enough to cause condensation or even frosting of the surface. The wet or frosted surface not only is a nuisance but can lead to more serious problems such as corrosion of the surface or damage to articles contacting the moisture.

A variety of insulation techniques and devices currently exist. One such device is a vacuum container in which the space between inner and outer walls is evacuated. This must be cylindrical and is relatively expensive, especially for larger containers. Glass vacuum systems are fragile, and stainless steel systems are even more costly. A variation of the vacuum approach is called multi-layered insulation where a layering of two or more polymer films separated by close placements of button-shaped members with a vacuum between the polymer films. This is suitable where flexibility is desired, for example for shaped surfaces, but not for a rigid, functional surface, and also is quite expensive.

Insulation is also commonly provided by packed fibers of glass or mineral, and blocks of closed-pore polymer such as polystyrene foam (e.g. Styrofoam™). The fibers or foams are used to prevent air circulation in the insulating space, since such circulation causes the air to convey heat between the walls bounding the space. Such insulation is economical and is used on containers for liquified gas, but it often is not sufficiently effective. For example, such containers using liquid nitrogen typically have condensation or frosting on the outside. Heating tape has been used for the outer surface to reduce the condensation, but this often is insufficient.

Another form of insulation, for more moderated temperatures, uses windows of the type commonly known as Thermopane™ with two or three panes of glass to enclose one or two spaces filled with a dry gas. These are designed for windows of buildings for visibility and passage of light, as well as to insulate the building interior from external hot or cold weather temperatures.

Certain calorimeters sometimes are adapted to utilize liquid nitrogen. These instruments are used for obtaining measurements on thermal characteristics of samples. One such calorimeter is a differential scanning calorimeter (DSC) for making measurements on a pair of samples in such a manner that a test sample is compared to another test sample or a reference sample, such as disclosed in U.S. Pat. No. 3,263,484. The samples are supported in an insulated container. A power supply provides power to each of the samples and temperatures are measured. In a DSC, differential power and temperature between samples are determined for comparison of heating characteristics such as phase changes. A furnace or other heating vessel is placed over the sample region for heating to provide a range of temperatures for the measurements. Liquid nitrogen, located in a reservoir below the sample support, may be used to extend DSC measurements to a lower temperature range. Such a system has used thick styrene foam blocks for insulation against the cold, but surface condensation has still been a significant problem, even with heating tape.

An object of the invention is to provide an improved system of thermal insulation for liquified gas such as liquid nitrogen. A further object is to provide such a system with reduced susceptibility to condensation of moisture on outer surfaces. A preferred object is to provide such a system incorporated into a calorimeter.

SUMMARY

The foregoing and other objects are achieved, at least in part, by a thermal insulating system for liquified gas, including a vessel with an inner chamber for containing a liquified gas at a low temperature relative to atmospheric temperature. The vessel comprises a plurality of walls arranged proximately in parallel, each pair of adjacent walls having a spacing to delimit a corresponding space. The walls include an inner wall, an outer wall and at least two partition walls disposed between the inner wall and the outer wall. The inner wall forms the inner chamber, and the outer wall is exposed to ambient atmosphere. Preferably there are two partition walls which more preferably are insulating walls. A closure means is located at boundaries of the walls so as Go enclose a gas in each space at substantially atmospheric pressure. Each spacing is selected to minimize heat transfer from the atmosphere to the inner chamber, and thereby minimize condensation of atmospheric vapor on the outer wall. Preferably each spacing is selected as essentially a maximum spacing for which convection of the gas in the corresponding space is substantially stagnant.

Advantageously the system further includes a cover for the vessel, the cover comprising a set of walls with spacings similar to those of the vessel. The partition walls of the cover preferably are self-supporting polymer sheet. The outer cover wall and partition walls of the cover preferably form a removable portion of the cover, and the inner cover wall is affixed to the vessel.

In a preferred aspect the system is in the form of a calorimeter in which a thermally conductive block is mounted on the vessel to extend into the inner chamber to contact the liquified gas, and a sample support is mounted in the block for supporting a sample for testing with the calorimeter. The cover of the calorimeter system includes a removable top cover positioned over the cap with at least one space delimited therebetween enclosing a gas at substantially ambient pressure. A sealing means is provided for sealing between the cover, the top cover and the block, thereby effecting thermal insulation over the block and the cap when the cover and top cover are closed.

DETAILED DESCRIPTION

The drawings illustrate features of the invention in a preferred embodiment which is a calorimeter incorporating liquified gas for low temperature cooling of samples. An example is a Perkin-Elmer model DSC-7 differential scanning calorimeter ("DSC") for comparing thermal characteristics of a pair of samples. This model, which in convention with similar instruments was equipped previously with thick styrene foam insulation, is adapted with replacement of the foam by the insulating system described herein. Although the invention is particularly advantageous with respect to a calorimeter, and is explained herein with respect to such a system, it will be appreciated that the invention should be useful for any container of cold liquified gas, such as a storage container, a transfer vessel or a conveying article such as tubing. As used herein and in the claims, the term "liquified gas" means the low temperature liquified phase of a substance that is gaseous at atmospheric temperature and pressure, such as liquid nitrogen, oxygen, hydrogen or helium. A specific objective is to provide insulation for no surface condensation in 80% humidity at 24° C.

Figure 2:
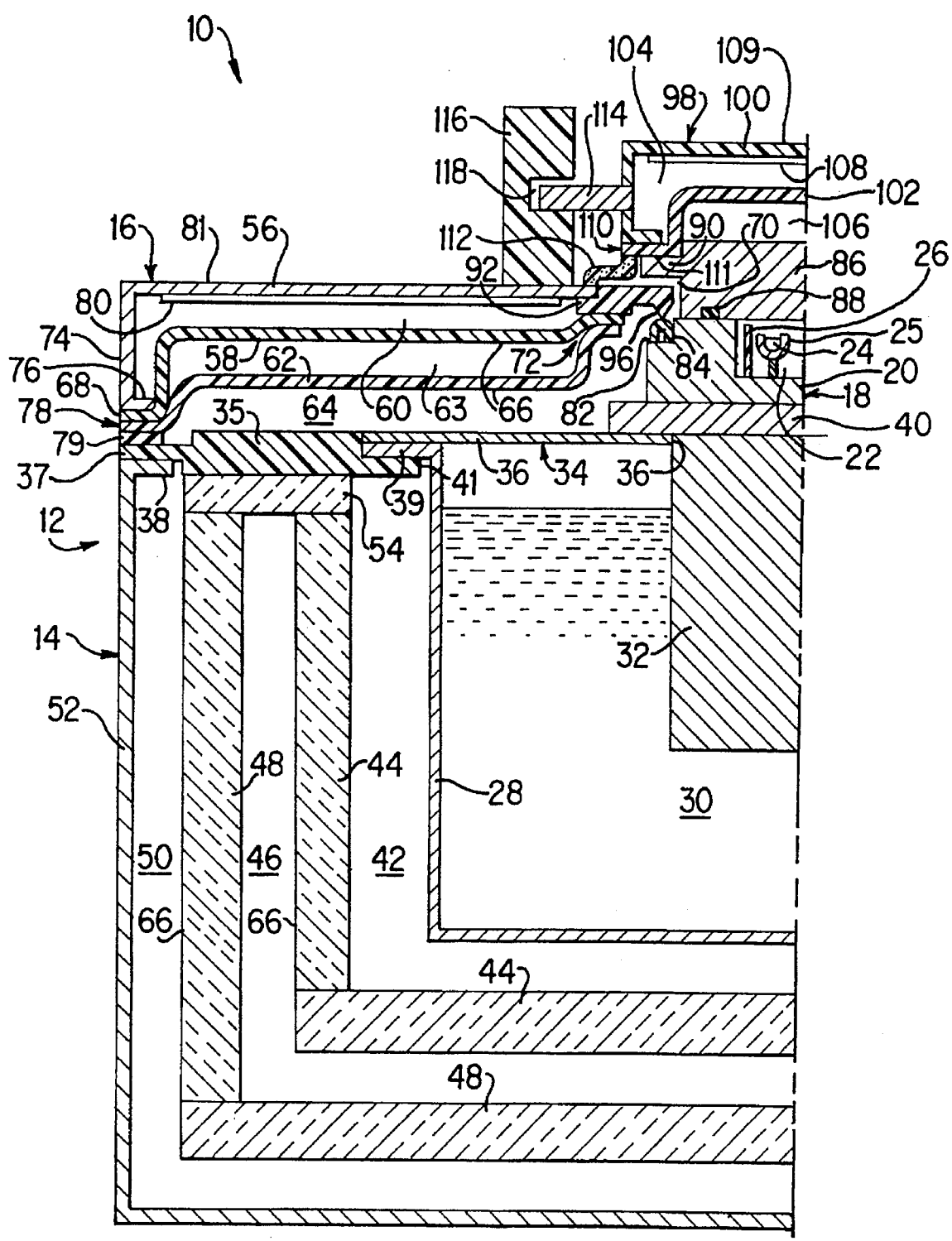
FIG. 2 is a symmetrical half section of the calorimeter container taken in the plane 2—2 of FIG. 1.

The calorimeter 10 has a container 12 that includes a vessel 14 with a removable cover 16 that may be hinged or lifted off. The calorimeter further includes a thermally conductive block 18 (FIG. 2), for example made of aluminum, having a sample section 20 with a cavity 22 open upwardly. In the manner disclosed in the aforementioned U.S. Pat. No. 3,263,484, one or two support cups 25 for samples 24 to be tested are mounted in the cavity. A furnace 26 typically surrounds the sample supports in the cavity for overall temperature control by a furnace power supply and controller (not shown). More direct temperature control and measurement are provided by a conventional system (also not shown) including heating elements and sensors in the supports connected to a differential power supply. The overall configuration of the calorimeter may be cylindrical or rectangular or a combination of both. For example, the container may be rectangular and the sample block cylindrical. The vessel portion and the cover portion of the container are formed of sets of walls with spaces for insulation according to the invention.

The vessel portion 14 of the calorimeter includes a bucket 28, generally metal such as aluminum, for holding a liquified gas 30 which typically is liquid nitrogen at 77 K. The block has a cooling member 32, preferably with vertical vanes (not shown) for increased surface area, extending downward from the sample section for contact with the liquid nitrogen, preferably by immersion, so as to provide cooling of the samples except when overridden by the furnace and support heaters. The vessel is formed, in part, by a metal shell 52 and a deck 34. The deck, in the present example, is formed of an outer ring 35 of fiberglass reinforced resin and an inner disk 36 (e.g. aluminum). The ring has an outer flange 37 resting on a lip 38 of the shell. The bucket has a flange 39 resting on a corresponding inner flange 41 of the ring. The inner disk rests over the bucket flange and is bounded by the upper portion of the fiberglass ring which extends a top surface outwardly. The inner disk extends inwardly over the bucket, and has a central opening for the cooling member.

The sample block, in the present case, includes an aluminum disk 40 bolted between the sample section and the cooling member, the disk being mounted on the deck to support the block. The sample block and deck are removable for maintenance. Other components of the vessel may be bonded, such attachments being standard such as bolts, rivets, welds or cement (glue).

The vessel 14 is further formed of a set of at least three, and preferably four spaced walls (or more as explained below) to provide insulation. The walls are arranged proximately to each other and in parallel. The bucket 28 containing the liquid nitrogen forms an inner wall. Outward of that wall and with a space 42 in between is a first partition 44. Further outward is a second space 46 and then a second partition 48. Next further outward is a third space 50 with the metal shell 52 (e.g. aluminum) of the vessel constituting the outer wall. The outer wall is exposed to ambient atmospheric conditions of temperature, pressure and humidity. These ordinarily are room temperature conditions, but may represent other situations such as out-of-doors, elevated altitude, under water, or the like.

Although the partitions 44, 48 in the vessel may be any suitable partitioning material, each of these partitions preferably is a block of insulating material such as Styrofoam™ generally having a thickness similar to the spacings to provide additional insulation. The insulating material actually should be as thick as practical within the volume constraints of the whole system, for example thickness similar to the spacings, but does not need to be nearly as thick as without the spacings. The set of four walls forms both the sides and the bottom of the vessel. For support, connecting blocks 54 of the foam are cemented over the tops of the partitions and to the bottom of a the outer wall flange.

The cover 16 preferably is also thermally insulating according to the invention. At least three, and preferably four (or more) walls are arranged proximately to each other and in parallel. Each pair of adjacent walls has a spacing so as to delimit a corresponding space therebetween, so that there are three (or more) such spaces. The cover walls include an outer cover wall 56, for example thin aluminum plate, and an inner cover wall oppositely disposed from the outer wall. This inner wall is formed by the deck 34 which is at least partially exposed to the inner chamber with the liquid nitrogen. Thus the cover actually is formed of a removable portion comprising its outer wall and the two partitions, and a fixed portion comprising the top and outer plates of the vessel. Two (or more) partition walls, advantageously of self-supporting polymer sheet, are disposed between the outer wall and the inner wall. Such partition formation has advantages of being light weight and readily shaped to desired configuration. The outer cover wall 56 and a first partition 58 delimit a first space 60, the first partition and a second partition 62 delimit a second space 63, and the second partition and the deck 34 delimit a third space 64.

More generally, the walls for the vessel and the cover may be formed of any rigid material (metal, ceramic, polymer or combination) depending on structural needs and other circumstances, and may have an insulating thickness as indicated above for the foam partitions in the vessel. A closure means is located at the boundaries of each set of walls so as to enclose a dry gas in each space at substantially ambient pressure. Although an inert gas such as nitrogen may be used in the spaces, air is generally suitable and should be dry if possible. The closures should, if possible, each be sealed to prevent seepage of outside humidity. Heat transfer preferably is reduced further by having a surface of at least one wall, and more preferably at least the partitions, be reflective of radiant heat. This may be effected, for example, by aluminizing by chemical vapor deposition (CVD), spraying aluminum paint, applying aluminum foil, or polishing if the wall is metal.

For the cover partitions 58, 62, molded polymer sheet, for example clear polyvinylchloride about 1 to 1.5 mm thick is suitable. Closures are formed conveniently for the cover partitions by molding flange lips 68 into the thick polymer sheet, the overlapping lips at the rectangular edges being cemented or bolted together. To accommodate the sample section 20 of the block 18, there is a central opening 70 in the cover, with similar end closures made by overlapping lips 72 at the hole. The outer metal wall 56 of the cover is formed downwardly at the sides 74, where it has an inward flange 76 adapted for closure to the corresponding lips 68 of the partitions. This assembly 78 forming the closure rests on a rubber gasket 79 affixed to the outer top plate of the vessel. A heating means such as an electric coil or, more suitably, an electric heating tape 80 (e.g. 3 watts) is cemented under the outer wall of the cover to heat the surface to further reduce condensation. In this case the outside surface 81 of the outer wall should be blackened to absorb infra-red radiation, such as with water base polonaise ceramic paint (which actually appears grey to the eye) with an emissivity of at least 0.6, to radiatively absorb heat from the room as much as practical to minimize the power requirements of the heating tape. The inwardly facing surface, including the tape surface, should be substantially reflective to minimize inward radiation of its heat to the next wall 58.

A preferred configuration is used for sealing the removable portion of the cover 16 to the sample block 18 to minimize heat flow in or out of the calorimeter. Near the upper edge of the block is a circumferential rim 82 facing upwardly, in this case recessed from the top. An insulating seal ring 84 of low thermal conductivity is positioned on the rim, the ring advantageously being a heat resistant polymer U-ring having an upside down U-shaped cross section. A removable cap 86 of material similar to that of the sample block is positioned on the sample block to cover and enclose the sample cavity 22, with an o-ring 88 to seal between the cap and the block. The cap has a circumferential flange 90 extending outwardly over the U-ring and spaced upwardly therefrom.

The cover 16 has its inner closure assembly 72 affixed to a generally flat polymer ring 92 extending inwardly from the closure. This extension ring alternatively may simply be an inward extension of the outer cover wall, although polymer is preferred for more insulation. The ring has a downward protuberance 96 of triangular cross section with an apex aimed downwardly to provide an airtight seal against the upside-down base of the "U" of the U-ring 84, generally in the space under the flange 90 of the cap. This closes off the lower space 64 under the movable portion of the cover when in closed position.

A top cover 98 is positioned over the cap. This is formed of an outer shell 100 of Delrin™ polymer or the like, and has at least one partition wall 102 similar to that in the main cover 16 to delineate a first space 104 with the outer shell. The cap 86 and the partition 102 in the top cover delimit a second space 106 therebetween. Although more would be more effective, only one partition should be needed as this region is removed from direct contact with the liquid nitrogen region. In a less effective version, the partition may be omitted to form only one space. The spaces should be established for optimum insulation in the same manner as for the cover and the vessel. A heating tape 108 is affixed under the shell, the shell has an emissive outer surface 109, for the same functions as those in the main cover.

The outer shell 100 and the partition 102 in the top cover are joined at a closure of outer flanges 110 forming a circumferential base 111 that rests on the flange 90 of the cap so as to position the top cover. Outwardly from the cap flange, a top seal ring 112, for example soft silicone rubber having a slanted "Z" cross section, is disposed between the base and the aluminum cover wall 56, cemented or otherwise affixed to either the cover wall or the base of the top cover, proximate the inner closure. This allows the top cover to be lifted away, so that the cap can be removed for servicing the samples in the holders, without removing the main cover 16. Thus the top cover is separately removable and, with the cover and the top cover in respective closed positions, closure is effected for the space 64 between the inner cover wall and its adjacent partition wall and for a space 106 in the top cover above the cap.

Figure 1:
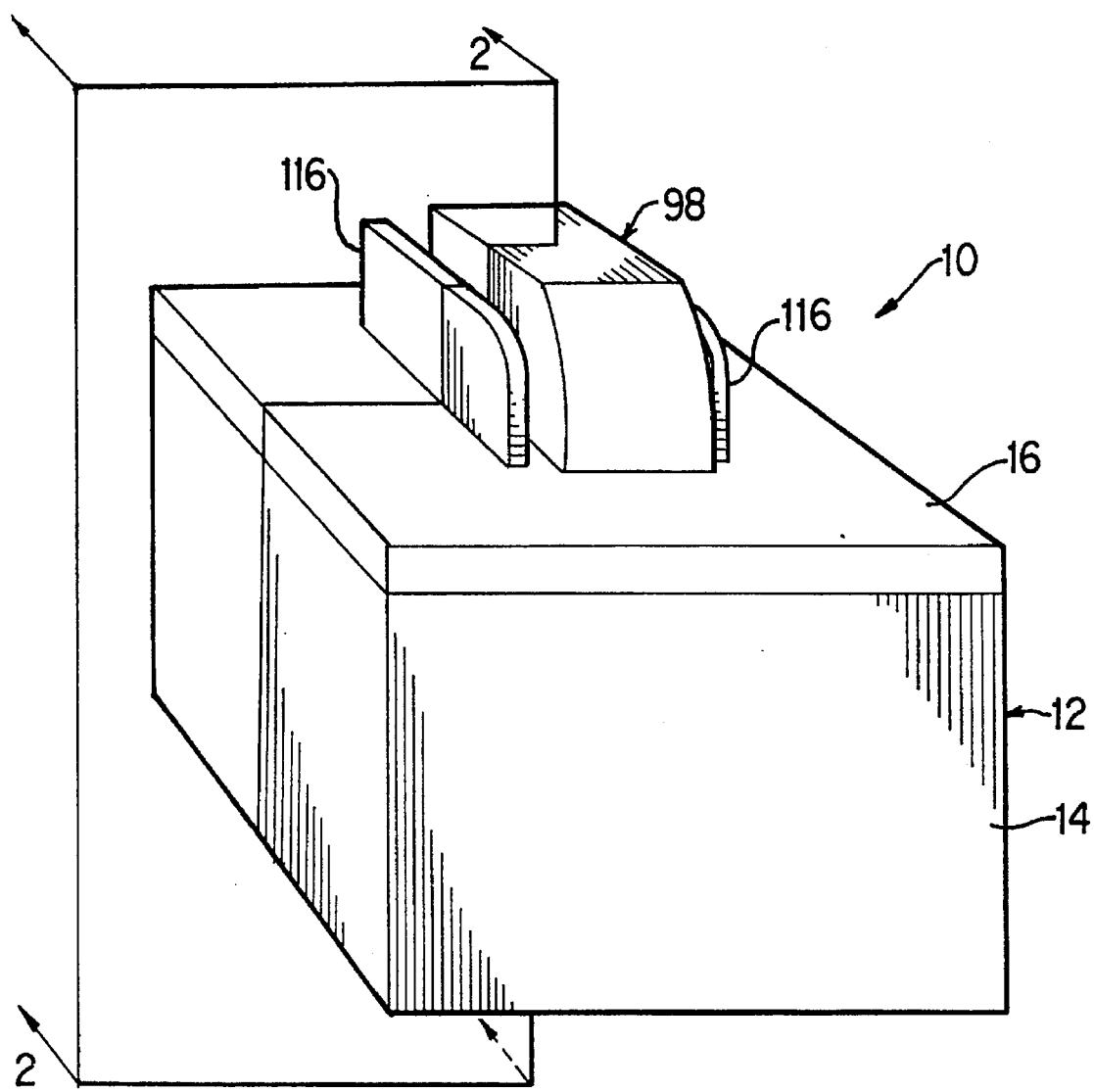
FIG. 1 is a perspective of a calorimeter container incorporating a thermal insulating system of the invention.

The top cover is held in place by conventional or other desired means, for example by pins 114 between a pair of upright supports 116 (FIG. 1) affixed to the main cover. The supports have slots 118 for the pin, the slots slanting upwardly (into the plane of the drawing) to allow upward sliding of the pins to lift and slide away the top cover.

The spacings between the walls in each section may be determined experimentally, but preferably are determined by heat transfer calculations. The spacings, including end spacings at the closures, each is selected to minimize heat transfer through the layers of walls and spacings. To do this, each spacing should be substantially the maximum spacing for which the gas in the corresponding space is substantially stagnant. Thermodynamic heat flow equations are used.

Greatest thermal resistances for the air (or other gas) layers occur when the free convective air movement over a surface or within a particular space is substantially stagnant with very little air movement. Under these quiescent conditions, air behaves as a stratified horizontal or vertical layer which effectively minimizes the exchange of heat and cold, forming excellent insulation barriers. For maximum thermal resistance, it also is required for the spacing to be as great as possible after the convection is substantially eliminated by reduced spacing to achieve optimum spacing. The method of the design is to iteratively vary the spacings, calculating a new thermal resistance with each iteration, and obtain essentially the highest resistance value possible.

As indicated above, radiation heat transfer preferably is minimized by reflection surfaces. Radiation will influence the temperatures at the walls, so the computations preferably should include this heat flow factor by using the standard Stefan-Boltzmann formula for all surfaces, including for reflecting surfaces.

The following examples are provided for three spaces, one side of the system being at liquid nitrogen temperature (77 K), and the other side at ambient atmospheric temperature of 22° C. (295 K). A surface temperature of the outer, atmospheric wall is estimated initially as 10.8° C. (283.8 K); this may be increased if heating tape is used. A mathematical model of the thermodynamic heat balances is created to determine the temperature conditions of each of the three layers of air with boundary temperatures T and spacings D of the walls and atmosphere:

Wall #1: $T_1=77$ K

Wall #2: Spaced $D_1$ from wall #1; $T_2=?$

Wall #3: Spaced $D_2$ from wall #2; $T_3=?$

Wall #4: Spaced $D_3$ from wall #3; $T_4=?$ (initially 282.8 K)

Ambient air at $T_5=295$ K.

The model starts with an assumed value for thermal resistance R, using $R=1/H \cdot A$ where H is film coefficient and A is surface area. Values for R and H depend upon a corresponding spacing D (which initially has an assumed value), and vary non-linearly with the temperatures being calculated, thus requiring iterations in the calculations. The unknown temperatures ($T_2$, $T_3$, $T_4$) for the walls at thermal equilibrium are calculated from R. This is achieved by equating heat flow Q per unit area for each section, and solving simultaneous equations:

$Q=(T_2-T_1)/R_1=(T_3-T_2)/R_2$ $Q=(T_3-T_2)/R_2=(T_4-T_3)/R_3$ $Q=(T_4-T_3)/R_3=(T_5-T_4)/R_4$

If an insulating wall such as styrofoam is used, the standard heat flow equation based on its thermal conductivity is included in the above heat flow equations. This will establish additional temperatures for each side of this wall.

Heating tape power, if used, is accounted for in the heat balance equations with an additional heat factor $Q_h$ for the outer wall, thus $(Q+Q_h)=(T_4-T_3)/R_3$.

Radiation in each stage is incorporated by making the R values depend upon a form of the Stefan-Boltzmann relationship. Thus for the first stage:

$R_1 = [1/R_{H1} + 1/R_{S1}]^{-1}$, where $R_{H1} = 1/H_1 \cdot A$ for the convective heat transfer as above, $R_{S1} = [\sigma \cdot f \cdot A \cdot (T_2^2 + T_1^2)(T_2 + T_1)]^{-1}$, for the radiation heat transfer, where σ is the Stefan-Boltzmann constant and f is a combination of the absorbtivity (one minus emissivity) for the relevant surface and a geometric shape factor that accounts for amount of radiation this surface sees from other surfaces.

Initially the coefficients R, based on initially selected spacings D, are estimated and temperatures are obtained. The wall temperatures T are then iterated upon with successive values of coefficients that are recalculated as described below, from the obtained wall temperatures. Each recalculated R establishes a new spacing D. Results are finalized when each temperature difference and its corresponding coefficient are within predetermined, acceptable error limits, for example 1% or less. This process is repeated for revised spacings ($D_1$, $D_2$, $D_3$) until an optimum is found for each of the three spacings, whereby $Q_h$ is minimal for the outer wall to be at a temperature that precludes condensation at 24° C. and 80% relative humidity.

A container will have both horizontal and vertical surfaces exposed to free convective ambient air, as well as horizontal and vertical spacings between walls. Different free convective heat transfer correlations exist for each type of surface and spacing, and these correlations are used to obtain the thermal resistance of the sides, bottom and top (main cover) of the container. The following are correlations for free convective heat transfer with examples for the three relevant conditions, where temperature dependent parameters for air are viscosity μ, thermal conductivity k, density δ and specific heat $C_p$. Each of these parameters depends on the average temperature $T_f$ in the space and is available from standard tables. An average temperature in the first space is assumed to be $T_f=(T_1+T_2)/2$, and the averages for the other spaces are defined similarly.

The following examples are given for the space between walls #1 and #2, with temperatures $T_1$ (which is 77 K) and $T_2$ (which is initially assumed and subsequently calculated iteratively). The thermal resistance R is determined for various correlations using thermodynamic numbers: Prandtl number is $Pr=C_p \cdot \mu/k$; and Grasshoff number Gr is as follows (for the first space):

$Gr = 9.807 \cdot \delta^2 \cdot (T_1-T_f)/T_f \cdot D^3/\mu^2$

Thermal resistance R is a function of D, Pr and Gr. Examples of correlations are set forth below. Computations including iterations and use of conditional statements are readily achieved by computer using standard mathematical programs. The example illustrates an interim step, and in each case values for D, H and R are determined and then used to iterate temperatures from the above heat flow equations. When iterations are completed, each spacing D is determined from the corresponding final R value.

Vertical Cavity

Assumed $T_2=170$ K, height of cavity L=0.157 m, spacing D=0.043 m; L/D=3.683. Relevant numbers are Pr=0.767, and Gr=2.291·10$^7$. The coefficient $H_v$ (in watts/meter$^2$-Kelvin [W/m$^2$K]) for a vertical cavity is:

When Gr=<6.0·10$^3$ then $H_v$=k/D=0.302.
When 6.0·10$^3$<Gr>=10$^{10}$, then $H_v = C \cdot k/D \cdot (L/D)^m \cdot [(Pr^2 \cdot Gr)/(0.2 \cdot Pr)]^n$;

For 1 < L/D =< 2,     C = 0.18, m = 0,      n = 0.29; or
For 2 < L/D < 10,    C = 0.22, m = 0.25,   n = 0.28; then $H_v$ = 6.422 (for 1 < L/D =< 2); or $H_v$ = 4.807 (for 2 < L/D < 10).

For L/D > 10, $H_v = 0.046 \cdot k/D \cdot (Gr \cdot Pr)^{0.333} = 0.153$

For present example, Gr=2.291·10$^7$, so $H_v$=4.807, and new D=48 mm.

Horizontal Cavity

Assumed $T_2=170$ K, length and width of cavity L=0.164 m, spacing D=0.025 m; L/D=6.572. Gr=2.291·10$^7$. The film coefficient $H_h$ for a horizontal cavity is:

For Gr=<3·10$^5$, $H_h$=k/D=0.456 (laminar or transition flow);
For Gr>3·10$^5$, $H_h$=0.043 Gr$^{0.25}$=2.142 (turbulent flow).

For present example, $H_h$=2.142, and D=0.025 m.

Vertical Surface

Assumed $T_4$ (outer wall) is 286 K. Relevant numbers are Pr=0.707, and Gr=6.464·10$^6$. (For deviation by angle θ up to 60° from vertical, the Gr equation is multiplied by cos θ.) The film coefficient $H_s$ for a vertical surface is:

For 10$^4$<Gr·Pr=<10$^{14}$, $H_{sv} = k/D \cdot \exp[0.3585 + 0.1139 \cdot \ln(Gr \cdot Pr) +$ $5.237 \cdot 10^{-3} \cdot \ln(Gr \cdot Pr)^2 - 3.092 \cdot 10^{-5} \cdot \ln(Gr \cdot Pr)^3]$.

For present example, Gr·Pr=4.557·10$^6$, so $H_{sv}$=3.186, and new D=201 mm.

Horizontal Surface

Assumed $T_4$ (outer wall) is 286 K. Relevant numbers are Pr=0.707, and Gr=1.699·10$^6$. The film coefficient $H_s$ for a horizontal surface is:

For 10$^{-5}$=<Gr·Pr=<10$^9$, $H_{sh} = k/D \cdot \exp[0.0672 + 0.1139 \cdot \ln(Gr \cdot Pr) +$ $5.720 \cdot 10^{-3} \cdot \ln(Gr \cdot Pr)^2 - 5.360 \cdot 10^{-5} \cdot \ln(Gr \cdot Pr)^3]$.

For present example, Gr·Pr=1.2012·10$^6$, so $H_{sh}$=2.758, and new D=129 mm.

Where several levels for each film coefficient H are available as indicated above, depending on Gr and the other factors, iterations should place H into the lowest level by reselecting spacing D. However, spacing D should otherwise be as great as possible consistent with the lowest H.

The table gives an optimum set of spacings that were determined for an insulating container according to the invention for liquid nitrogen. The overall size of the container was 30 cm by 30 cm by 17 cm high, with an inner bucket 21 cm by 21 cm by 12 cm high. Spacings are from $D_1$ nearest the cold wall. The vessel and cover were configured as described in detail above. Surface treatments using reflective aluminum foil according to mil spec MIL-T-23397B-II was adhered to the outer side of the inner partition. copper & Brass Sales Inc. ANO-FOL™ #715-38 was adhered to the inner side of the inner partition and the outer side of the outer partition. In the cover, an aluminum CVD coating with a protective clear coat was applied to the inside of the tape, the top side of the outer polymer sheet partition, and the under side of the inner polymer partition. The outer surface was painted with Powder Coat Paint Co. No. 464-360#4 TEX for an emissivity of 0.87. Dimensions in the table for D and foam thickness are in mm, and for H are in watts/m2K.

TABLE

|  | Sides | Bottom | Cover | Top Cover |
| --- | --- | --- | --- | --- |
| Spacing $D_1$ | 6.85 | 6.35 | 25.0 | 25.0 |
| Coef. $H_1$ | 4.80 | 6.81 | 2.14 | 2.76 |
| Foam Thickness | 12.7 | 12.7 | (none) | (none) |
| Spacing $D_2$ | 12.7 | 12.7 | 12.0 | 3.68 |
| Coef. $H_2$ | 2.06 | 4.65 | 3.48 | 3.68 |
| Foam Thickness | 12.7 | 12.7 | (none) | (none) |
| Spacing $D_3$ | 6.35 | 6.35 | 7.0 | (none) |
| Coef. $H_3$ | 3.85 | 3.85 | (none) | (none) |

This system has allowed use of the calorimeter without any condensation of water on the outside surface except in occasional high humidity conditions (85% and over). This compared with the previous system of a larger container with styrofoam 15 cm (6 inches) thick (without such air spacings) on which substantial areas of condensation were routinely experienced. Even with the occasional condensation in high humidity, the amount of surface water was substantially reduced.

Thus it has been ascertained that three spaces, between four walls, are quite sufficient for insulating against liquid nitrogen. Four or five spaces (up to six walls) are incrementally better, but the improvements are small, added thickness becomes a disadvantage, and computations are more complex, so there is a diminishing return. Therefore, the normally preferred number of walls is four, providing for three spaces which were found to be surprisingly effective.

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

What is claimed is:

1. A thermal insulating system Including a vessel having an inner chamber for containing a liquified gas at a low temperature relative to atmospheric temperature, the vessel comprising:

a plurality of walls arranged proximately In parallel, each pair of adjacent walls having a spacing to delimit a corresponding space; the walls including an inner wall, an outer wall and at least two partition walls disposed between the inner wall and the outer wall, the inner wall forming the inner chamber, and the outer wall being for exposure to ambient atmosphere;

closure means located at boundaries of the walls so as to enclose each space between the walls; and a gas in each space at substantially atmospheric pressure, wherein each spacing is selected to minimize heat transfer from the atmosphere to the Inner chamber, and thereby minimize condensation of atmospheric vapor on the outer wall.

2. The system of claim 1 wherein the plurality is between four and six inclusive.

3. The system of claim 2 wherein the plurality is four.

4. The system of claim 1 wherein each spacing is selected as substantially a maximum spacing for which the gas in the corresponding space is substantially stagnant.

5. The system of claim 1 wherein at least one of the walls has a surface reflective of radiant heat.

6. The system of claim 5 wherein each of the partition walls has a surface reflective of radiant heat.

7. The system of claim 1 wherein at least one of the walls is an insulating wall.

8. The system of claim 7 wherein each of the partition walls is an insulating wall.

9. The system of claim 8 wherein each of the partition walls has a surface reflective of radiant heat.

10. The system of claim 1 further comprising a cover for the vessel, the cover comprising:

a further plurality of walls arranged proximately in parallel, each pair of adjacent walls of the cover having a further spacing to delimit a corresponding further space, the walls of the cover including an inner cover wall, an outer cover wall and at least two further partition walls disposed between the inner cover wall and the outer cover wall, the inner cover wall being at least partially exposed to the inner chamber, and the outer cover wall being for exposure to the atmosphere; and further closure means located at boundaries of the walls of the cover so as to enclose a gas in each further space at substantially atmospheric pressure, wherein each further spacing is selected to minimize heat transfer from the atmosphere to the inner chamber, and thereby minimize condensation of atmospheric vapor on the outer cover wall.

11. The system of claim 10 wherein the plurality is between four and six inclusive.

12. The system of claim 11 wherein the plurality is four.

13. The system of claim 10 wherein each spacing is selected as substantially a maximum spacing for which the gas in the corresponding space is substantially stagnant.

14. The system of claim 10 wherein at least one of the walls has a surface reflective of radiant heat.

15. The system of claim 14 wherein each of the partition walls has a surface reflective of radiant heat.

16. The system of claim 10 wherein the partition walls of the cover are formed of self-supporting polymer sheet.

17. The system of claim 16 wherein each of the partition walls of the cover has a surface reflective of radiant heat.

18. The system of claim 17 further comprising heating means for heating the outer cover wall to further minimize condensation of atmospheric vapor on the outer cover wall, the outer cover wall having an outwardly facing surface outward of the heating means, the outwardly facing surface having an emissivity of at least 0.6, and the heating means having an inwardly facing surface substantially reflective of radiant heat.

19. The system of claim 10 further comprising heating means for heating the outer cover wall to further minimize condensation of atmospheric vapor on the outer cover wall, the outer cover wall having an outwardly facing surface outward of the heating means, the outwardly facing surface having an emissivity of at least 0.6, and the heating means having an inwardly facing surface substantially reflective of radiant heat.

20. The system of claim 10 wherein the outer cover wall and the further partition walls form a removable portion of the cover, and the inner cover wall is affixed to the vessel.

21. The system of claim 10 in the form of a calorimeter.

22. The system of claim 21 further comprising a thermally conductive block mounted on the vessel to extend into the inner chamber for contacting the liquified gas, and a sample support mounted on the block for supporting a sample for testing with the calorimeter, the block having a central cavity open upwardly with the sample support mounted therein, wherein the system further comprises a cap positioned over the block to enclose the cavity, and the cover further comprises a removable top cover positioned over the cap with at least one cap space delimited therebetween enclosing a gas at substantially atmospheric pressure, and sealing means for sealing between the cover, the top cover and the block, thereby effecting thermal insulation over the block and the cap.

23. The system of claim 22 wherein each cap space is selected to minimize heat transfer from the atmosphere to the block, and thereby minimize condensation of atmospheric vapor on the top cover.

24. The system of claim 23 wherein the block has a circumferential rim facing upwardly, the inner cover wall is affixed to the vessel, the outer cover wall and the further partition walls form a removable portion of the cover and are joined in an inner closure so as to form a central opening in the cover, the top cover has a circumferential base surface, and the sealing means comprises an insulating seal ring disposed on the circumferential rim, an inward extension from the inner closure with a downward protuberance that is urged against the insulating seal ring when the removable portion of the cover is in closed position and is lifted from the insulating seal ring when the removable portion of the cover is in opened position, and a top seal ring disposed on the outer cover wall proximate the inner closure such that the base surface of the top cover is urged against the second seal ring when the top cover is in closed position and is lifted away from the outer cover wall when the top cover is in opened position, whereby the top cover is separately removable and, with the cover and the top cover in respective closed positions, closure is effected for the space between the inner cover wall and its adjacent partition wall and for the space in the top cover above the cap.

25. The system of claim 24 wherein the insulating seal ring is a polymer ring having an upside down U-shaped cross section.

* * * * *